US008932862B2

(12) United States Patent
Chait et al.

(10) Patent No.: US 8,932,862 B2
(45) Date of Patent: Jan. 13, 2015

(54) METHOD FOR MEASURING SOLUBILITY

(75) Inventors: Arnon Chait, Bay Village, OH (US); Boris Y. Zaslavsky, Solon, OH (US)

(73) Assignee: Analiza, Inc., Bay Village, OH (US)

( * ) Notice: Subject to any disclaimer, the term of this patent is extended or adjusted under 35 U.S.C. 154(b) by 2053 days.

(21) Appl. No.: 10/779,164

(22) Filed: Feb. 13, 2004

(65) Prior Publication Data

US 2004/0229375 A1 Nov. 18, 2004

Related U.S. Application Data

(63) Continuation of application No. PCT/US02/26019, filed on Aug. 16, 2002.

(60) Provisional application No. 60/313,196, filed on Aug. 16, 2001.

(51) Int. Cl.
*G01N 31/00* (2006.01)
*G01N 21/64* (2006.01)
*G01N 21/76* (2006.01)
*G01N 21/75* (2006.01)

(52) U.S. Cl.
CPC ............... *G01N 21/75* (2013.01); *G01N 21/76* (2013.01)
USPC ............... 436/2; 436/106; 436/114; 436/119; 436/123; 436/146; 436/72

(58) Field of Classification Search
USPC .............. 436/106, 114, 119, 123, 146, 172, 2
See application file for complete search history.

(56) References Cited

U.S. PATENT DOCUMENTS

| | | | |
|---|---|---|---|
| 5,008,204 A | 4/1991 | Stehling | |
| 5,241,072 A | 8/1993 | Colon et al. | |
| 5,340,474 A | 8/1994 | Kauvar | |
| 5,734,024 A | 3/1998 | Zaslavsky | |
| 5,769,074 A | 6/1998 | Barnhill et al. | |
| 5,818,231 A | 10/1998 | Smith | |
| 5,948,750 A | 9/1999 | Garsky et al. | |
| 6,136,960 A | 10/2000 | Chait et al. | |
| 7,011,955 B1 | 3/2006 | Stemmler et al. | |
| 7,247,498 B2 * | 7/2007 | Godec et al. | 436/180 |
| 7,968,350 B2 | 6/2011 | Chait et al. | |
| 2001/0016590 A1 | 8/2001 | Ahotupa et al. | |
| 2002/0145425 A1 | 10/2002 | Ebbels et al. | |
| 2003/0162224 A1 | 8/2003 | Chait et al. | |
| 2004/0229375 A1 | 11/2004 | Chait et al. | |
| 2004/0236603 A1 | 11/2004 | Heller et al. | |
| 2006/0240416 A1 | 10/2006 | Banerjee et al. | |
| 2006/0255257 A1 | 11/2006 | Belgovskiy et al. | |
| 2006/0269964 A1 | 11/2006 | Chait et al. | |
| 2007/0128618 A1 | 6/2007 | Chait et al. | |
| 2008/0050831 A1 | 2/2008 | Chait et al. | |

FOREIGN PATENT DOCUMENTS

| | | |
|---|---|---|
| WO | WO 99/10522 A1 | 3/1999 |
| WO | WO 00/10674 A1 | 3/2000 |
| WO | WO 01/55698 A1 | 8/2001 |
| WO | WO 03/016883 A1 | 2/2003 |
| WO | WO 03/042694 A2 | 5/2003 |
| WO | WO 2004/111655 A1 | 12/2004 |
| WO | WO 2005/008247 A2 | 1/2005 |
| WO | WO 2005/008247 A3 | 1/2005 |
| WO | WO 2006/124100 A2 | 11/2006 |
| WO | WO 2007/027561 A2 | 3/2007 |
| WO | WO 2008/005043 A2 | 1/2008 |

OTHER PUBLICATIONS

Office Action from U.S. Appl. No. 11/641,611 dated Apr. 5, 2011.
Office Action from U.S. Appl. No. 13/110,345 dated Aug. 5, 2011.
Office Action from U.S. Appl. No. 13/110,345 dated Dec. 6, 2011.
Office Action from Australian Application No. 2006345702 dated Oct. 10, 2011.
Office Action from Australian Application No. 2006345702 dated Jan. 25, 2012.
Office Action from Canadian Application No. 2,466,663 dated Oct. 17, 2011.
Office Action from Canadian Application No. 2,528,535 dated Nov. 23, 2011.
Office Action from Chinese Application No. 20068005677.3 dated Oct. 27, 2011.
Office Action from Canadian Application No. 2,528,535 dated Jul. 23, 2012.
Office Action from Chinese Application No. 200680052677.3 dated Jul. 4, 2012.
Office Action from European Application No. 04 776693.6 dated Mar. 9, 2012.
Arnoldi et al., "Lipophilicity—Antifungal Activity Relationships for Some Isoflavonoid Phytoalexins", *Journal of Agricultural and Food Chemistry*, vol. 38, No. 3, 1990, pp. 834-838.
Harboe, et al., "Generation of Antibodies to the Signal Peptide of the MPT83 Lipoprotein of Mycobacterium Tuberculosis", *Scandinavian Journal of Immunology*, vol. 55, No. 1, Jan. 2002, pp. 82-87.
Kohwi et al., "Amphipathic Lipid-Bound Protein Antigens in Mouse Bladder Carcinomas Detected by a Monoclonal Antibody", *Biochemistry*, vol. 23, No. 25, 1984 pp. 5945-5950.
Müller et al., "Real and Pseudo Oxygen Gradients in Ca-Alginate Beads Monitored During Polarographic $PO_2$-Measurements Using Pt-Needle Microelectrodes", *Biotechnology and Bioengineering*, vol. 44, No. 5, 1994, pp. 617-625.
International Search Report/Written Opinion, dated Nov. 23, 2004, for PCT/US2004/019343, filed Jun. 14, 2004.
Zaslavsky, "Aqueous Two-Phase Partitioning" (Book) Marcel Dekker, New York, Ch. 1-10 (1995).

(Continued)

*Primary Examiner* — Jan Ludlow
(74) *Attorney, Agent, or Firm* — Wolf, Greenfield & Sacks, P.C.

(57) ABSTRACT

A method of determining the solubility of a compound in a selected solvent is provided that does not require determination of, or use of, standards having known concentrations of the compound. In one aspect, the method can include preparation of a mixture where not all of a compound is dissolved in the provided solvent, separating undissolved compound from the solvent, and direct determination of the amount of the compound dissolved in the solvent. Methods adapted for use include those where a multiplicity of compounds or solvents are tested in parallel. Devices adapted for these methods are also provided by the present disclosure.

52 Claims, 6 Drawing Sheets

(56) References Cited

OTHER PUBLICATIONS

Everberg et al., "Protein pre-fractionation in detergent-polymer aqueous two-phase systems for facilitated proteomic studies of membrane proteins," *J Chromatogr* A (2004) 1029:113-124.
Office Action from U.S. Appl. No. 10/293,959 dated Jul. 17, 2007.
Office Action from U.S. Appl. No. 10/293,959 dated Jun. 25, 2008.
Office Action From U.S. Appl. No. 10/293,959 dated Apr. 28, 2009.
International Search Report and Written Opinion for PCT/US2006/048344 (filed Dec. 19, 2006) dated Apr. 24, 2008.
Chait, A. "From Structure to Signature," 8th Annual SBS Conference & Exhibition, Sep. 22-26, 2002, Netherlands Congress Centre, The Hague, The Netherlands.
Chait, A. "HTS Technology for Analysis of Structural Signatures of Biomolecules: Methodology and Applications," California Separation Science Society, WCBP 2002, 6th Symposium on the Interface of Regulatory and Analytical Sciences for Biotechnology Health Products, Jan. 27-30, 2002.
Platt, D.E. et al., "QSAR in grossly underdetermined systems: Opportunities and issues," IBM Journal of Research and Development, vol. 45, 2001 (web page).
QSAR Introduction (web pages; pub. date unknown).
Richon, A. et al., "An Introduction to QSAR Methodology," (web page; pub. date unknown).
Office Action mailed Jun. 29, 2006 from U.S. Appl. No. 10/293,959.
Office Action mailed Dec. 5, 2006 from U.S. Appl. No. 10/293,959.
International Search Report from International Application No. PCT/US02/26019, filed Aug. 16, 2002.
International Preliminary Examination Report from International Application No. PCT/US02/26019, filed Aug. 16, 2002.
Written Opinion from International Application No. PCT/US02/26019, filed Aug. 16, 2002.
International Search Report from International Application No. PCT/US02/36519, filed Nov. 12, 2002.
Albertsson, P.A., et al., "Separation processes in biotechnology," Bioprocess Technology, vol. 9, pp. 287-327, 1990.
Andrews, A.T., et al. "Affinity gel electrophoresis as a predictive technique in the fractionation of transgenic sheep milk proteins by affinity aqueous two-phase partitioning," Biotechnology Letters, vol. 22, pp. 1349-1353, 2000.
Atktinson, L, et al., "Trypsin and alpha-chymotrypsin partitioning in polyethylene glycol/maltodextrin aqueous two-phase systems" Food and Bioproducts Processing, 1994, 72 (C2):106-112.
Berggren, K. et al., "Substitutions of surface amino acid residues of cutinase probed by aqueous two-phase partioning," Biochimica et Biophysica Acta, vol. 1481, pp. 317-327, 2000.
Bevan et al. A High-Throughput Screening Method for the Determination of Aqueous Drug Solubility Using Laser Nephelometry in Microtiter Plates. Analytical Chemistry, Apr. 15, 2000, vol. 72, No. 8, pp. 1781-1787.
Guiliano, K.A., "Aqueous two-phase protein partitioning using textile dyes as affinity ligands," Analytical Biochemistry, vol. 197, No. 2, pp. 333-339, 1991.
Gulyaeva, N., et al., "Relative hydrophobicity of organic compounds measured by partitioning in aqueous two-phase systems," Journal of Chromatography B, vol. 743, pp. 187-194, 2000.
Kuboi, R., et al., "Evaluation of surface hydrophobicities of proteins using hydrophobic interaction with nonionic surfactants in aqueous two-phase partitioning systems," Kagaku Kogaku Ronbunshu, vol. 19, No. 3, pp. 446-454, 1993.
Sakurai A., et al., "Ligand and nuclear factor-dependent change in hydrophobicity of thyroid hormone [beta] 1 receptor," Thyroid, vol. 8, No. 4, pp. 343-352, 1998.
Takano et al. Solubility Measurement of Liquid Organic Compounds in Water, Nippon Kagaku Kaishi, 1985, vol. 11, pp. 2116-2119. Chemical Abstract No. 105:60254. CAS Online, Columbus, Ohio.
Zaslaysky, A., et al., "A New Method for Analysis of Components in a Mixture without Preseparation: Evaluation of the Concentration Ratio and Protein-Protein Interaction," Analytical Biochemistry, vol. 296, pp. 262-269, 2001.
Program listing of the Society of Biomoecular Screening 2002, Session 2A Technical Program for the 8th Annual SBS Conference & Exhibition, Sep. 22-26, 2002, Netherlands Congress Centre, The Hague, The Netherlands.
Program listing of the Well-Characterized Biologics Conference 2002, California Separation Science Society, WCBP 2002, 6th Symposium on the Interface of Regulatory and Analytical Sciences for Biotechnology Health Products, Jan. 27-30, 2002.
Stovsky, M., et al. "PSA/SIA: A New Highly Sensitive and Specific Structure-Based Assay for Prostate Cancer" (presentation), AUA NC 82nd Annual Meeting, Chicago, IL, Sep. 24-27, 2008.
Sniegoski, P., "An Examination of the Concentration of Organic Components Water-Extracted From Petroleum Products" Waters Research, vol. 9, pp. 421-423; 1975.
Takano, Japanese Chemistry Association Journal, 1985 (11), pp. 2116-2119.
Yan, X, "Detection by Ozone-Induced Chemiluminescence in Chromatography" Journal of Chromatography A, 842 (1999), pp. 267-308.
Office Action from European Application No. 04776693.6 dated May 11, 2010.
Office Action from U.S. Appl. No. 11/818,911 dated Jun. 23, 2010.
Office Action from U.S. Appl. No. 10/293,959 dated Jul. 7, 2010.
Durand et al. "Protein Glycosylation and Diseases: Blood and Urinary Oligosaccharides as Markers for Diagnosis and Therapeutic Monitoring" Clinical Chemistry 46:6, pp. 795-805 (2000).
Guzzetta "Reverse Phase HPLC Basics for LC/MA" An IonSource Tutorial, published Jul. 22, 2001.
Peracaula et al. "Altered glycosylation pattern allows the distinction between prostate-specific antigen (PSA) from normal and tumor origins" Glycobiology, vol. 13, No. 6, pp. 457-470, 2003.
Schena et al. "Parallel human genome analysis: Microarray-based expression monitoring of 1000 genes" Proc. Natl. Acad. Sci. vol. 93, pp. 10614-10619, Oct. 1996.
Singh et al. "Gene expression correlates of clinical prostate cancer behavior" Cancer Cell: Mar. 2002, vol. 1, pp. 203-209.
Office Action from U.S. Appl. No. 11/818,911 dated Dec. 6, 2010.
Office Action from U.S. Appl. No. 11/641,611 dated Jan. 5, 2011.
Zaslavsky, J. "Characteristics of Protein-Aqueous Medium Interactions Measured by Partition in Aqueous Ficoll-Dextran Biphasic System," J. Chromatogr., 1983, 260:329-336.
Office Action from U.S. Appl. No. 11/641,611 dated Sep. 1, 2010.
Bodnar, et al., "Exploiting the Complementary Nature of LC/MALDI/MS/MS and LC/ESI/MS/MS for Increased Proteome Coverage," *J. Am. Soc. Mass. Spectrom* 2003, 14, 971-979.
Office Action in Canadian Application No. 2,466,663 dated May 6, 2010.
Office Action in Canadian Application No. 2,528,535 dated Mar. 15, 2010.
Office Action European Application No. EP 06851492 dated Mar. 31, 2009.
Office Action European Application No. EP02768567 dated Mar. 24, 2009.
Office Action Canadian Application No. 2,528,535 dated May 5, 2009.
Office Action European Application No. 04776693 dated Oct. 10, 2008.
Office Action European Application No. 04776693 dated Oct. 15, 2007.
Office Action European Application No. 02795636 dated Nov. 14, 2005.
Office Action European Application No. 02795636 dated Feb. 8, 2007.
Office Action European Application No. 02795636 dated Oct. 27, 2008.
Takano et al. "Measuring the Solubility of Liquid Organic Compounds in Water" Journal of the Chemical Society of Japan, 1985, (11), pp. 2116-2119.

* cited by examiner

METHOD FOR MEASURING SOLUBILITY

RELATED APPLICATIONS

This application is a continuation of International Application No. PCT/US02/26019, filed Aug. 16, 2002, which was published under PCT Article 21(2) in English, and claims priority to U.S. Provisional Application Ser. No. 60/313,196, filed Aug. 16, 2001. Both application are incorporated herein by reference.

FIELD OF THE INVENTION

In general, the disclosed invention is directed to methods allowing determination or estimates of the miscibility, solubility or other similar properties of compounds in selected or chosen solvents. More particularly, the invention relates in part to methods for facilitating measurements of the solubility of organic, inorganic and organo-metallic compounds, particularly of compounds related to pharmaceutical and agrochemical research and development.

BACKGROUND

In technical fields relating to chemical formulation of compounds, such as, but not limited to the fields of pharmaceutical and agrochemical research and development, it is almost always necessary to evaluate the general suitability of a newly developed drug candidate prior to launching into full development. Such an evaluation of the general suitability or, in the field of pharmaceutical development, drug-ability of such chemical compounds typically includes solubility studies of the compound in various solvents as well as solubility profiles at various pH values. However, carrying out such studies for a great many compounds can be problematic and resource-intensive. At the earlier stages of the drug discovery process, in particular, the solubility measurements are generally performed for a large variety of compounds. Furthermore, many of these compounds are only available in limited quantities, either due to difficulties in manufacturing larger quantities, handling all but the smallest sized samples, or simply because the cost of producing or handling larger quantities of the compounds is not feasible.

However, simply bypassing the solubility studies is also not a viable option for product development as selection of an otherwise suitable candidate compound that does not have a suitable solubility profile can cause significant problems. Indeed, insoluble or poorly soluble compounds often prove difficult to develop into drugs. Even with significant motivation, the development of low-solubility drugs is more time-consuming and expensive than for a compound with otherwise more suitable properties.

Traditionally, "equilibrium" solubility has been determined by agitating or shaking the compound with the solvent of choice for at least 24 hours or until no more of the compound will dissolve, then filtering, and determining the concentration of dissolved compound by a suitable analytical assay. These analytical assays had to be calibrated, a process which includes preparation of at least several solutions of the known varied concentrations of the compound (standard solutions), and establishing a quantitative relationship between a measurable analytical signal and the compound concentration. This approach is inappropriate in a modern drug discovery setting. The throughput, number of unknown samples that can be determined in a given amount of time or using a given quantity of resources, such as machines, personnel, samples, and the like, is not high enough to meet the required demand to analyze a great number of potential lead compounds. For example, determination of the mass of samples and/or standards presents too restrictive a checkpoint in the process for maintaining the high throughput desired as the process of weighing hundreds (or thousands) of solid samples in submilligram quantities.

Therefore, to alleviate the perceived hindrances to high throughput analysis of compounds, those of skill in the art have sought to develop improved methods for determining solubility of compounds. One of these methods is based on measuring turbidity of an aqueous media after adding a fixed amount of solution of a compound in dimethyl sulfoxide (DMSO) by using laser nephelometry (Bevan & Lloyd, "A high-throughput screening method for the determination of aqueous drug solubility using laser nephelometry in microtiter plates," *Anal. Chem.* 72, 1781-1787 (2000)). However, this method is limited in that it does not allow one to measure solubility of compounds in pure aqueous media without DMSO. Another method suggested in the literature is based on measuring the vapor pressure depression for a solution of the compound at saturation (Parikh et al., "Rapid solubility determination using vapor-phase osmometry," *J. Biomol. Screen.* 4, 315-318 (1999)). However, this method is limited to use for measuring the solubility of nonionic compounds with rather good solubility in pure water. Furthermore, it cannot be used for poorly soluble compounds, and its use for solutions of ionic compounds in buffer or salt solutions is considered questionable (Parikh et al., "Rapid solubility determination using vapor-phase osmometry," *J. Biomol. Screen.* 4, 315-318 (1999)).

Additional methods, such as those available from pIon Inc., are based on producing experimental samples by mixing DMSO solution of a compound of interest with a given aqueous solvent, incubation of the mixture for a fixed period of time, removing the precipitant formed by filtration, and assaying the compound concentration by measuring the optical absorbance of the filtrate at the maximum wavelength specific for the compound. However, differences between these assays and those to determine the concentration of compounds to use or to determine the optical absorbance values to use in these additional methods give rise to difficulties. For example, a concentration assay (similar to those used to determine solubility, but without incubation and filtration) is performed in a separately prepared mixture of the same DMSO solution of the compound with the same aqueous solvent but using a higher ratio of DMSO to aqueous solvent in the mixture. Under suitable conditions, the higher DMSO/aqueous solvent ratio is such that the compound is not precipitated out of solution. Correspondingly, the measurement of absorbance is taken to indicate the absorbance for a given quantity of the compound. This measurement when all the compound is solubilized, or rather, sets of these measurements are used as reference points to generate a relationship between the measured absorbance value and the quantity of compound. In determine the relationship, essentially a standard curve as is known in the art, the linearity of the optical absorbance vs. concentration over the used DMSO/aqueous solvent ratio range is assumed. Comparison of the standard curve and the measured value determined from the experimental sample, following incubation and filtration, is used to calculate/determine the concentration of the compound in the experimental sample.

In general, procedures like those available pIon have additional disadvantages which limit their practical application under some circumstances. In particular, the technique as outlined above requires that it be possible to determine the initial concentration of a compound under study in DMSO or in a DMSO-containing solvent. Further, this method is limited to compounds with chromophoric groups, such that they can be detected by absorbance measurements. Procedures that do not require that the compounds to be amenable to their initial concentration being determined in DMSO or a similar solvent or that do not require that the compounds have easily detectable or commonly used chromophoric groups would be a significant advancement of the technology to test the solubility of compounds.

The present invention provides new methods for determining the solubility of compounds of interest in solvents of interest. In specific embodiments, this includes methods that allow measurement of the solubility of organic, inorganic and organo-metallic compounds, particularly of compounds related to pharmaceutical research and development, in aqueous media with or without organic solvent. Further, the provided method is not necessarily limited by the ionization state of the compound or by the presence of inorganic salts and/or buffer salts in the media. Further, the provided methods are adaptable for high-throughput automated measurements. These and other objectives of the invention will become apparent in view of the detailed description below.

SUMMARY OF THE INVENTION

In accordance with the purpose(s) of this invention, as embodied and broadly described herein, this invention, in one aspect, relates to a process of measuring the solubility of a compound in a selected solvent, comprising the steps of: preparing a mixture of a quantity of the compound with a volume of the selected solvent; incubating the mixture of compound and solvent, whereby compound can dissolve in the solvent to form a solution of the compound; removing undissolved compound from the mixture, thereby providing a quantity of the solution of the compound; determining the amount of a selected constituent of the solution of the compound resulting from removing undissolved compound from the mixture, wherein the determination does not include a comparison of physical properties of one or more solutions containing known concentrations of the compound and physical properties of the solution of the compound; and calculating the solubility of the compound in the selected solvent by determining the amount of the compound present in a determined quantity of the solution of the compound.

In a second aspect, the present invention relates to a method for determining the solubility of chemical compounds, including organic, inorganic and organo-metallic compounds. The method can include: preparing a mixture of unknown excess amount of compound sample with a fixed volume of a solvent of choice; maintaining a sample of the aforementioned mixture until thermodynamically equilibrated phase separation occurs; withdrawing aliquots of the saturated solution from the thermodynamically equilibrated mixture; analyzing the concentration of the compound in the solution in aliquots withdrawn from the saturated solution by measuring the overall content of a given chemical element in a fixed volume of the solution; and converting the overall content of a given chemical element in the solution into the concentration of the tested compound from the molar content of the chemical element in the compound, and the detector-specific universal quantitative relationship between the element content and quantity of the element-containing compound in a fixed solution volume.

In a third aspect, the present invention relates to a method for determining the solubility of one or more compounds in one or more selected solvents. The method can include preparing two or more mixtures of compound and solvent and determining the solubility of each according to any method according to the first and second aspects of the invention.

In a fourth aspect, the present invention relates to an apparatus for determining the solubility of a compound in a selected solvent. The apparatus can include: a mixing device that combines a quantity of a compound with a volume of a selected solvent, thereby forming a mixture in a container; an incubating device that maintains the mixture at determined conditions for, optionally, a determined period of time; a separating device that removes undissolved compound from the mixture, thereby providing a quantity of a solution of the compound; and a detector that detects the amount of a selected constituent in the solution of the compound. The apparatus can be adapted to any method according to the first, second or third aspects of the invention.

In certain embodiments, the present invention is directed to a process of measuring solubility of organic, inorganic and organo-metallic compounds, particularly of compounds related to pharmaceutical, cosmetic, and agrochemical research and development, in aqueous media without organic solvent not limited by ionization state of the compound or the presence of inorganic salts and/or buffer salts in the media and adaptable for a high-throughput automated measurements. In certain embodiments, the method used can be based on dispersing an unknown-weight quantity of a compound in a solvent of choice by shaking, sonication, or other means, removing the non-dissolved compound by filtration, centrifugation, or other means, and measuring total amount of a constituent present in the dissolved compound molecule. Constituents detected and measured can include, but are not limited to, particular moieties, groups, or chemical elements, such as nitrogen, carbon, or sulfur.

BRIEF DESCRIPTION OF THE DRAWINGS

The following is a brief description of drawings, which form a portion of the specification, and are presented for the purpose of illustrating selected aspects of the invention. The drawings are incorporated in the specification and together with the description serve to explain the principles of certain aspects of the invention.

DETAILED DESCRIPTION OF THE INVENTION

Figure 1:
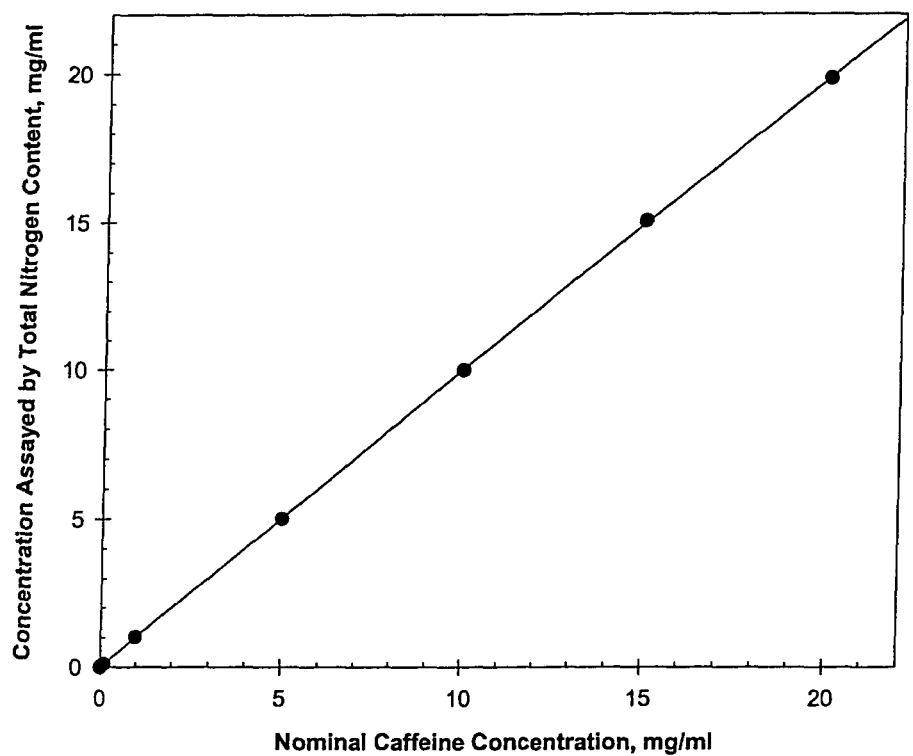
FIG. 1 illustrates the relationship between the concentration of caffeine in solution measured by the total nitrogen content of the solution and the nominal concentration values for the prepared caffeine solutions.

Before the present compounds, compositions, articles, devices, and/or methods are disclosed and described, it is to be understood that this invention is not limited to specific methods, specific solutions, or to particular devices, as such may, of course, vary. It is also to be understood that the terminology used herein is for the purpose of describing particular embodiments only and is not intended to be limiting. Throughout the specification and claims, reference will be made to a number of terms which shall be defined to have the following meanings:

As used in the specification and the appended claims, the singular forms "a," "an" and "the" include plural referents unless the context clearly dictates otherwise. Thus, for example, reference to "solvent" includes mixtures of solvents, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

In certain contexts, solubility of a compound in a solvent media is defined as the compound concentration in the solvent at saturation. In other contexts, solubility of a compound in a selected solvent can be defined as the compound concentration in solution under specified conditions wherein the quantity of the compound in contact with the solution is not a significantly limiting factor (for instance, where a solid compound is added to a solvent and solid compound remains undissolved after a specified period of time). In another context, solubility of a compound can mean determination that under specified conditions, or that after following a specified procedure, the compound remains in solution at the specified concentration. If solubility of the compound is used in this context, the determined solubility of the compound relates to a limit of the compound's solubility, namely, that the compound must at least be soluble at the determined concentration, although it can be possible to have higher concentrations of the compound in solution. Use of such determinations can provide adequate characterization of a compound's characteristics in regard to its ability to dissolve in a particular solvent or to remain in solution with a particular solvent to be used as guidelines in developing protocols or processes as will be recognized by those of skill in the art.

The measurement of the solubility of a compound includes a number of steps, including the preparation of a saturated solution of the compound and measuring the quantity of the compound present in the solution. In the use of standard methods; the preparation of a saturated solution requires weighing out a given quantity of dry compound into a vessel and adding a fixed amount or volume of a solvent, dispersion of the compound in the solvent, removing the non-dissolved fraction of the compound, and measuring the quantity of the dissolved compound in the remaining solution.

As normally practiced, preparation of the saturated solution (particularly, weighing out the compound and adding a fixed amount of solvent) and measuring the quantity of dissolved compound present in solution remaining after removing nondissolved compound require most of the time and manpower. In part, this is due to the fact that the dispersion of compound can be performed in parallel for a multiple set of samples by shaking, sonication, mixing, and the like and that removing nondissolved compound can be performed in parallel for a multiple set of samples by filtration, centrifugation, and the like.

When assaying the solubility of even a small number of compounds, standard methods can often require weighing of hundreds of solid samples, generally in sub-milligram quantities. Further, the step of measuring the quantity of dissolved compound in the remaining solution following removal of nondissolved compound generally requires the use of an analytical assay that is commonly compound-specific. Whenever the assay is compound specific, separate assay development for each compound to be studied can be required. This requirement for extensive assay development can cause excessive expenditure of resources.

In one aspect, the present invention relates to the method of measuring the solubility of a compound in a selected solvent that includes the steps of preparing a saturated solution of the compound, wherein the saturated solution is prepared by combining a quantity of compound with a volume of the selected solvent, wherein the volume of selected solvent is not adequate to fully solubilize the compound and measuring the amount of compound solubilized in a given quantity of the resulting solution. The method can include the steps of: combining a quantity of the compound with a volume of solvent; incubating a volume of the combined compound and solvent for a period of time, optionally with action to disperse the compound in the volume; removing undissolved compound from at least a portion of the resulting solution of dissolved compound in the solvent; and determining the quantity of compound dissolved in a quantity of solvent.

The compound whose solubility is tested can be in solid, liquid or gaseous form, or a combination of these forms. For example, a slurry of a compound in another solvent can be provided to a solvent for which the solubility of the compound is to be tested.

The amounts of compound provided can vary in accordance with the necessary requirements imposed by the materials tested. For example, when testing compounds of very high solubility in a given solvent, the quantity of material provided relative to the volume of solvent provided will necessarily be greater than is needed when compounds of very low solubility in a given solvent are tested. Thus, quantities of compounds used can be greater than 1, 2, 5, 10, 30, 100, 250, 500 or 1000 pico-, nano-, micro- or milli-grams or less than 1, 2, 5, 10, 30, 100, 250, 500 or 1000 pico-, nano-, micro- or milli-grams. Thus, volumes of solvent used can be greater than 1, 2, 0.5, 10, 30, 100, 250, 500 or 1000 nano-, micro- or milli-liters or less than 1, 2, 5, 10, 30, 100, 250, 500 or 1000 nano-, micro- or milli-liters. As recognized by those of skill in the art, solvents can be a combination of one or more compounds (i.e., a solvent can be absolution).

The process or step of dissolving/suspending sample can be one step or it can be more than one step. For example, the sample can be suspended in a smaller volume of a solvent and then provided to a larger volume of a second solvent (for example, as a slurry or as an agitated suspension). Alternatively, the compound can be dissolved in a first solvent and then provided to a second solvent in which the compound may not be fully soluble. For example, a quantity of a compound can be dissolved in a small volume of organic solvent and then added to a volume of an aqueous solvent whereupon at least a portion of the compound comes out of solution. For example, if the organic solvent remains in the solution during the subsequent measurement, the solubility can be taken to mean kinetic or apparent solubility which may or may not correspond to "equilibrium" solubility. These measurements can be used for high throughput comparison of compound to order or to rank their apparent solubility. In some embodiments wherein the compound is suspended or dissolved and then added to a further solvent, the first solvent can be a volatile solvent that can removed from a solution formed by addition of any further solvent. In such embodiments, the removal of the first volatile solvent can cause at least a portion of the compound suspended or dissolved in the first solvent to come out of solution. Measurement of the amount of compound remaining in the solvent remaining at the end of incubation can thereby allow measurement of the solubility of the compound in the remaining solvent.

Dispersion of compound throughout at least a portion of a volume of solvent can be facilitated by stirring, shaking, sonication, as well as by other forms of mechanical agitation as are known to those of skill in the art. Such efforts to effect or increase dispersion can be continuous throughout the desired incubation or can be intermittent.

Incubation of mixtures of compound and solvent can be conducted for lengths of time that are appropriate for the particular compounds and solvents used, as well as other conditions which impact solubility, such as, but not limited to temperature and pressure. Incubation can be at temperatures greater than −25, −15, −10, −5, −2, 0, 2, 5, 10, 15, 20, 25, 30, 35, 40, 50, 60, 80 or 100° C. or less than −25, −15, −10, −5, −2, 0, 2, 5, 10, 15, 20, 25, 30, 35, 40, 40, 60, 80, or 100° C. Incubation can be at pressures greater than 0.1, 0.2, 0.3, 0.4, 0.5, 0.6, 0.7, 0.8, 0.9, 1.0, 1.1, 1.2, 1.3, 1.4, 1.5, 1.6, 1.8, 2.0, 3, or 5 atmospheres or at pressures less than 0.1, 0.2, 0.3, 0.4, 0.5, 0.6, 0.7, 0.8, 0.9, 1.0, 1.1, 1.2, 1.3, 1.4, 1.5, 1.6, 1.8, 2.0, 3, or 5 atmospheres.

Following incubation, removal of undissolved compound from the volume of solvent and dissolved compound can be removed. Methods that can be used to remove undissolved compound include those relying on mechanical entrapment, such as filtration, and those relying on differences in the properties of the dissolved compound/solution and undissolved compound, such as centrifugation or sedimentation.

Thus, according to certain aspects of the invention, the procedure of providing a quantity of compound and a volume of solvent for preparing a saturated solution is simplified and does not require the most time- and labor-consuming part, namely, the process of weighing samples. Instead, the procedure used for distributing a quantity of compound need only include transfer of a quantity of the compound that into a vessel that is greater than the amount of compound that can be brought into solution by the provided volume of solvent. Consequently, the amount of the sample need only be defined loosely as exceeding a specified value as can be determined by one of skill in the art. A trial and error process can be used to determine that the amount of compound used is adequate or that the volume of solvent is not too great by determining that a quantity of compound remains undissolved following incubation to dissolve the compound. In certain embodiments, the present invention allows use of small quantities of a sample, such as one of approximately 0.01, 0.02, 0.05, 0.1, 0.2, 0.3, 0.5, or 1.0 mg, or as one that consists of but a visible quantity of a dry sample on a spatula. The procedure to dispense small quantities of compound can be automated, for example, as dry powder dispensing in a given amount of time under fixed spatula vibration settings and the like.

Detection of the presence of dissolved compound in a solution is also provided by the present invention. The method of detection utilized can be a method that is easily automated. According to certain aspects of the present invention, the detection procedure can consist of measuring total content of a chemical element present in a portion of solvent containing the compound that is present in the molecule of the compound (such as carbon, nitrogen, sulfur, etc.). For example, detection of the amount of carbon present in an aqueous solution of sugar can be used to determine the concentration of sugar present in a volume of sugar. In specific embodiments, the determination will include measurement of the amount of an element in a fixed volume of a compound solution. The measurement of the selected element can be performed with a universal equimolar chemiluminescent nitrogen detector, equimolar chemiluminescent sulfur detector, or total organic carbon detector. In specific embodiments, the element detected can be an element present in the compound that is not present in the solvent alone. For example, the detection of carbon in the use of the method to determine the amount of sugar present in an aqueous solution of sugar. In other specific embodiments, the element detected can be an element present in both the element and the solvent and the determination of the amount of the element present in a specific volume of solution can be used to determine the quantity of the compound dissolved in the solution, thereby allowing determination of the solubility of the compound. Alternatively, in other embodiments, the measurement of the amounts of more than one element can be measured, wherein the ratio of the elements indicates the amount of compound dissolved in the solution.

Alternatively, in other embodiments, the amount of an element present in the compound and the amount of a second element present in the solvent can be used to determine the relative amount of compound present in a given aliquot relative to the amount of solvent. In these embodiments of the invention, the measurement of the volume of solution measured need not be measured in any manner independent of determining the amount of elements present in the measured sample.

Detection, measurement or determining the amount of selected constituent present in a solution of the compound can include comparison with values determined from solutions having a known concentration. Alternatively, the detection, measurement or determining the amount of a selected constituent of a solution of a compound can exclude comparison of physical properties of solutions containing known concentrations of the compound and physical properties of the solution of the compound, namely, the method can be conducted without the use of standards composed of known amounts or known concentrations of the compound whose concentration is being determined.

In other embodiments of the invention, an apparatus which includes; a mixing device that can combine a quantity of compound with a volume of solvent to form a mixture in a container; an incubating device that can maintain the mixture at determined conditions for, optionally, a determined time; a separating device that can remove undissolved compound from the mixture to provide a quantity of the solution of the compound; and a detector that can detect the amount of a selected constituent in the solution of the compound. Other particular embodiments of devices adapted to conducting the methods of the invention are those that are recognized by those of skill in the art as being capable of conducting the presently disclosed methods. These particular embodiments of devices include those adapted for automated handling and treatment of samples according the methods of the present invention.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Measuring Concentration of Solutions of Caffeine of Varied Concentrations by Measuring Total Nitrogen Content in a Fixed Volume of the Caffeine Solution Caffeine was purchased from Sigma Chemical Company (St. Louis, Mo., USA) and used without further purification. Solutions of caffeine in water were prepared at the nominal concentrations from 0.9 up to 83.37 mg/ml. Five of these solutions had unidssolved residue and were filtered through 0.45μ filter. These solutions were injected in triplicate into chemiluminescent nitrogen detector (model 8060, Antek Instruments) equiped with an analytical loop of 0.5 μl volume. The results obtained are presented in FIG. 1.

The concentrations for the examined caffeine solutions are plotted in FIG. 1 versus the nominal concentration values for the prepared solutions. The data given in FIG. 1 indicate clearly that the absolute concentrations determined by measuring total nitrogen content in a fixed volume of solution provides the right values for concentrations of the compound.

Example 2

Measuring Solubility of Different Compounds by the Procedure According to the Present Invention Allopurinol, bendroflumethiazide, butamben, clofazimine, hydroflumethiazide, nifedipine, nitroflurantoin, nitroflurazone, perphenazine, phenacetin, tolazamide, and sulfanilamide were purchased from Sigma Chemical Company (St. Louis, Mo., USA) and used without further purification. About 10 mg quantities of each of these compounds were mixed with 0.5 ml of water, and shaken for 24 hrs. at room temperature. Undissolved residue in each solution was removed by filtration through 0.45μ filter, and the solutions were injected in triplicate into chemiluminescent nitrogen detector (model 8060, Antek Instruments) equipped with an analytical loop of 5 μl volume.

Figure 2:
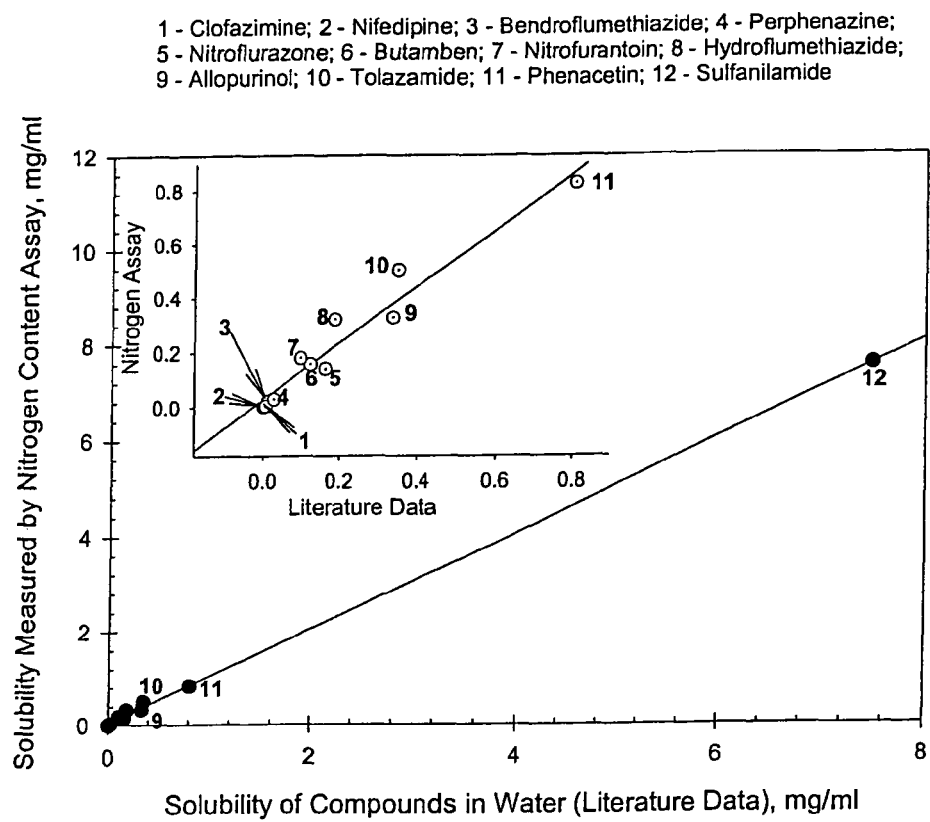
FIG. 2 illustrates the relationship between the solubility values obtained according to the present invention and the literature solubility data.

The measured nitrogen content for each compound solution was transformed into concentration units, and the resulting experimental solubility values are plotted in FIG. 2 versus corresponding literature solubility data for the compounds examined. The plot presented in FIG. 2 may be described by a linear relationship as:

$$S_{exp} = 0.036(\pm 0.018) + 1.005(\pm 0.008) \cdot S_{lit},$$

N=12; r2=0.9993; s=0.0596, where $S_{exp}$ is the compound solubility measured experimentally by the procedure described; $S_{lit}$—solubility of the compound reported in the literature; N is the number of compounds; r—correlation coefficient, s—standard error of estimate.

The data given in FIG. 2 indicate clearly that there is a good correlation between the solubility values obtained by the procedure according the present invention and the literature data for different compound with solubility over the range from 1 μg/ml up to ca.10 mg/ml.

The results illustrated by the above examples demonstrate that the procedures according to the present invention facilitate high-throughput measurements of solubility for a wide variety of compounds.

Example 3

Figure 3:
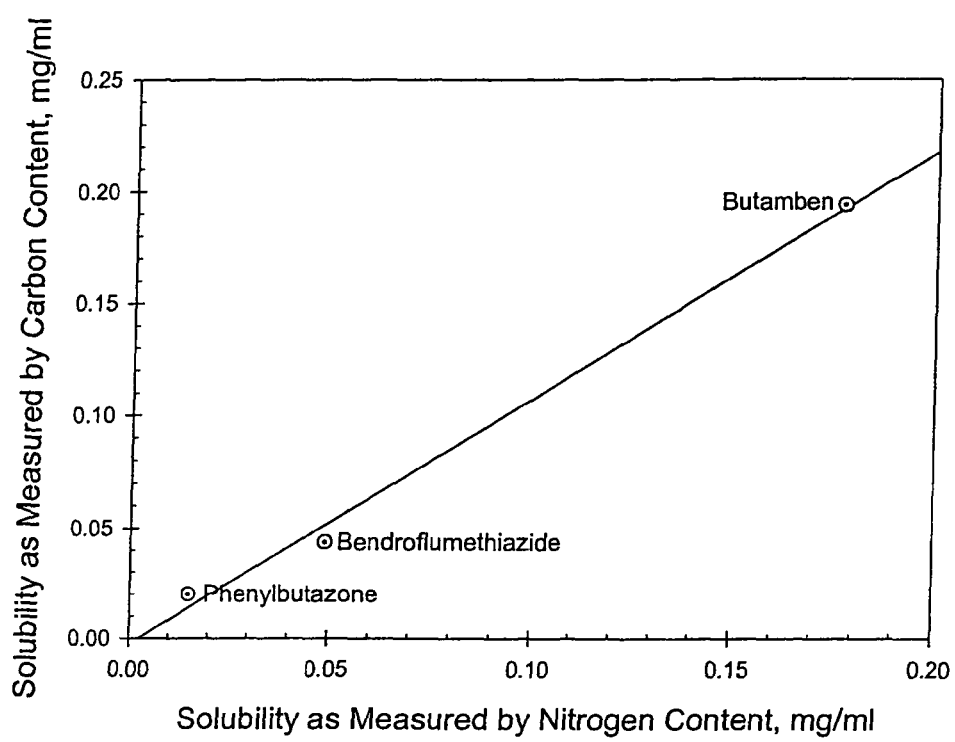
FIG. 3 illustrates the relationship between the solubility data obtained for different compounds according to the present invention as measured by the total nitrogen content of the saturated solution in water and as measured by the total carbon content of the saturated solution in water.

Measuring Solubility of Several Different Compounds in Water by the Procedure According to the Present Invention Using Two Different Assay Protocols Butamben, bendroflumethiazide, and phenylbutazone were purchased from Sigma Chemical Company (St. Louis, Mo., USA) and used without further purification. About 20 mg quantities of each of these compounds were mixed with 10.0 ml of water, and shaken for 24 hrs. at room temperature. Undissolved residue in each solution was removed by filtration through 0.45μ filter. The filtered solutions were separated into two parts. One part of each solution was injected in triplicate into chemiluminescent nitrogen detector (model 8060, Antek Instruments) equipped with an analytical loop of 5 μl volume. The other part of each filtered solution was assayed with total organic carbon analyzer (model TOC-5000, Shimadzu Scientific Instruments, Columbia, Md., USA). Results obtained by analysis of both nitrogen content and carbon content of the saturated solutions are presented in FIG. 3. The results presented in FIG. 3 indicate that there is a good correlation between the data obtained by the two assays.

The results of this example illustrate that the assaying of an element content in the saturated solutions of compounds allows one to measure the compound concentrations, i.e. solubility of compounds, independent of the particular element content measured.

Example 4

Figure 4:
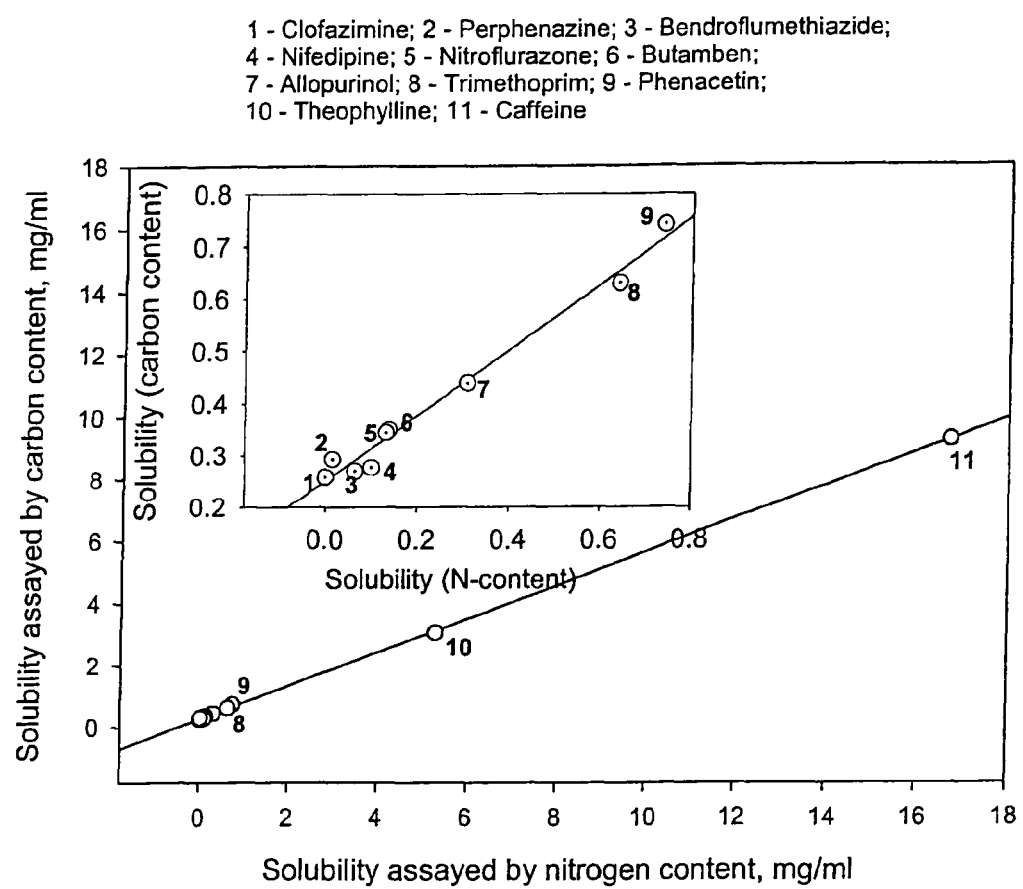
FIG. 4 illustrates the relationship between the solubility data obtained for different compounds according to the present invention as measured by the total nitrogen content of the saturated solution in buffer at pH 7.4 and as measured by the total carbon content of the saturated solution in buffer at pH 7.4.

Measuring Solubility of Several Different Compounds in Buffer by the Procedure According to the Present Invention Using Two Different Assay Protocols Allopurinol, bendroflumethiazide, butamben, clofazimine, nitroflurazone, theophylline, nifedipine, perphenazine, phenacetin, trimethoprim, and caffeine were purchased from Sigma Chemical Company St. Louis, Mo., USA) and used without further purification. About 20 mg quantities of each of these compounds were mixed with 10.0 ml of 0.15M NaCl in 0.01M universal buffer, pH 7.4 composed of appropriate quantities of acetic acid, phosphoric acid, boric acid, and NaOH, and shaken for 24 hrs. at room temperature. Undissolved residue in each solution was removed by filtration through 0.45μ filter. Parts of the filtered solutions were injected in triplicate into chemiluminescent nitrogen detector (model 8060, Antek Instruments) equipped with an analytical loop of 5 μl volume. The other part of each filtered solution was assayed with total organic carbon analyzer (model TOC-5000, Shimadzu Scientific Instruments, Columbia, Md., USA). Results obtained by analysis of both nitrogen content and carbon content of the saturated solutions are presented in FIG. 4. The results presented in FIG. 4 indicate that there is a good linear correlation between the data obtained by the two assays.

The results of this example illustrate that the assaying of an element content in the saturated solutions of compounds allows one to measure the compound concentrations, i.e. solubility of compounds, independent of the particular element content measured.

Example 5

Measuring Solubility of Different Compounds Dissolved in DMSO by the Procedure According to the Present Invention Allopurinol, bendroflumethiazide, butamben, clofazimine, nitroflurazone, theophylline, nifedipine, perphenazine, phenacetin, sulfanilamide, and trimethoprim were purchased from Sigma Chemical Company. (St. Louis, Mo., USA) and used without further purification. Stock solutions of each compound in DMSO with the concentration of 5.0 mg/ml were prepared. The fixed volume of 450 µl of 0.01M universal buffer containing 0.15M NaCl, pH 7.4 was mixed with 9.2 µl of stock DMSO solution of each compound. The mixtures were shaken for 24 hrs. at room temperature. Undissolved residue in each solution was removed by filtration through 0.45µ filter, and the solutions were injected in triplicate into chemiluminescent nitrogen detector (model 8060, Antek Instruments) equipped with an analytical loop of 5 µl volume.

Figure 5:
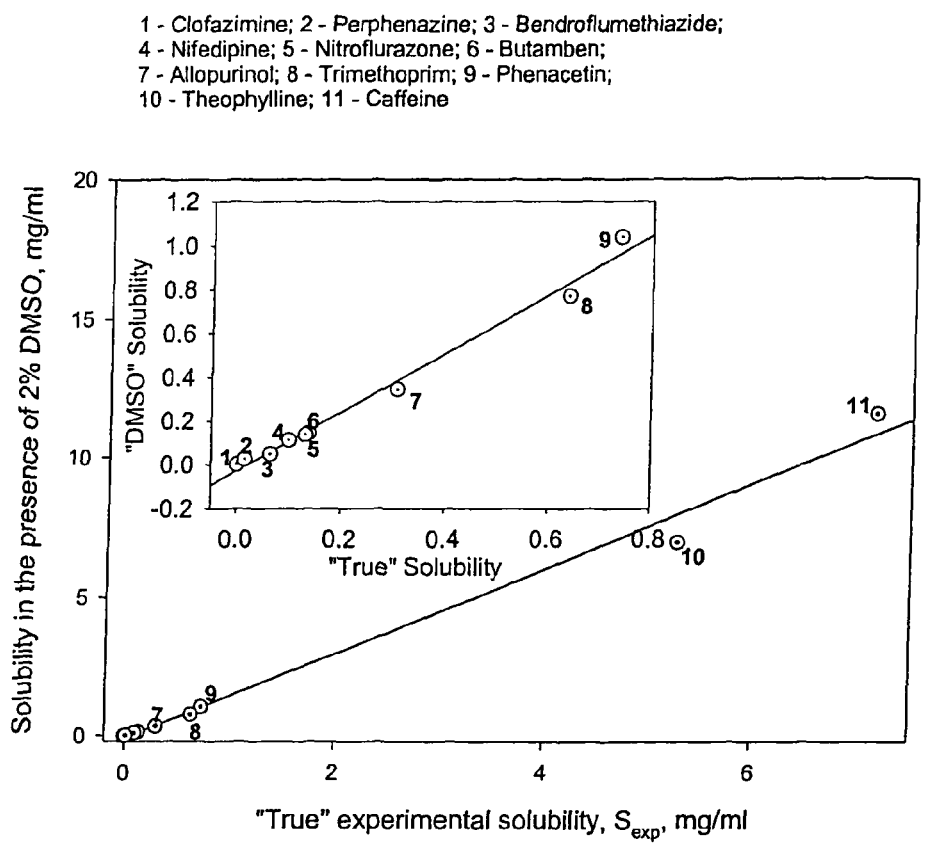
FIG. 5 illustrates the relationship between the solubility data in the presence of 2% DMSO obtained for different compounds according to the present invention as measured by the total nitrogen content of the saturated solution and the solubility of the same compounds without DMSO.

The measured nitrogen content for each compound solution was transformed into concentration units, and the resulting experimental "DMSO solubility" values are plotted in FIG. 5 versus corresponding data obtained for the same compounds in the same buffer using the procedure described in Example 2. The data given in FIG. 5 indicate clearly that there is a good correlation between the "DMSO solubility" values obtained by the procedure and those obtained with dry compounds obtained by the procedure according to the present invention over the range from 1 µg/ml up to ca.10 mg/ml. The correlation between the data may be described by a linear relationship as:

$$S_{exp}^{DMSO}=-0.10(\pm 0.15)+1.524(\pm 0.054)*S_{exp}$$

N=11; $r^2$=0.9887; s=0.4244, where $S_{exp}$ is the compound solubility measured experimentally by the procedure described; $S_{exp}^{DMSO}$—solubility of the compound measured in the presence of DMSO; N is the number of compounds; r—correlation coefficient, s—standard error of estimate.

The above correlation indicates clearly that the solubility of compounds examined in the presence of DMSO generally exceeds that of the same compounds without DMSO. However, the linear relationship observed can be used to re-calculate the measured solubility values from $S_{exp}^{DMSO}$ into $S_{exp}$ values, or used for ranking the solubility of a studied series of compounds.

This example illustrates the possibility to use the procedures according to the present invention for compounds dissolved in an organic solvent, such as DMSO, for estimating the compound solubility in a given aqueous solution.

Example 6

Ranking Solubility of Different Compounds by the Procedure According to the Present Invention Allopurinol, bendroflumethiazide, butamben, clofazimine, nitroflurazone, theophylline, nifedipine, perphenazine, phenacetin, trimethoprim, and caffeine were purchased from Sigma Chemical Company (St. Louis, Mo., USA) and used without further purification. Stock solutions of each compound in methanol with the concentration of 5.0 mg/ml were prepared. The fixed volume of 450 µl of 0.01M universal buffer containing 0.15M NaCl, pH 7.4 was mixed with 9.2 µl of stock methanol solution of each compound. The mixtures were shaken for 24 hrs. at room temperature. Undissolved residue in each solution was removed by filtration through 0.45µ filter, and the solutions were injected in triplicate into chemiluminescent nitrogen detector (model 8060, Antek Instruments) equipped with an analytical loop of 5 µl volume.

Figure 6:
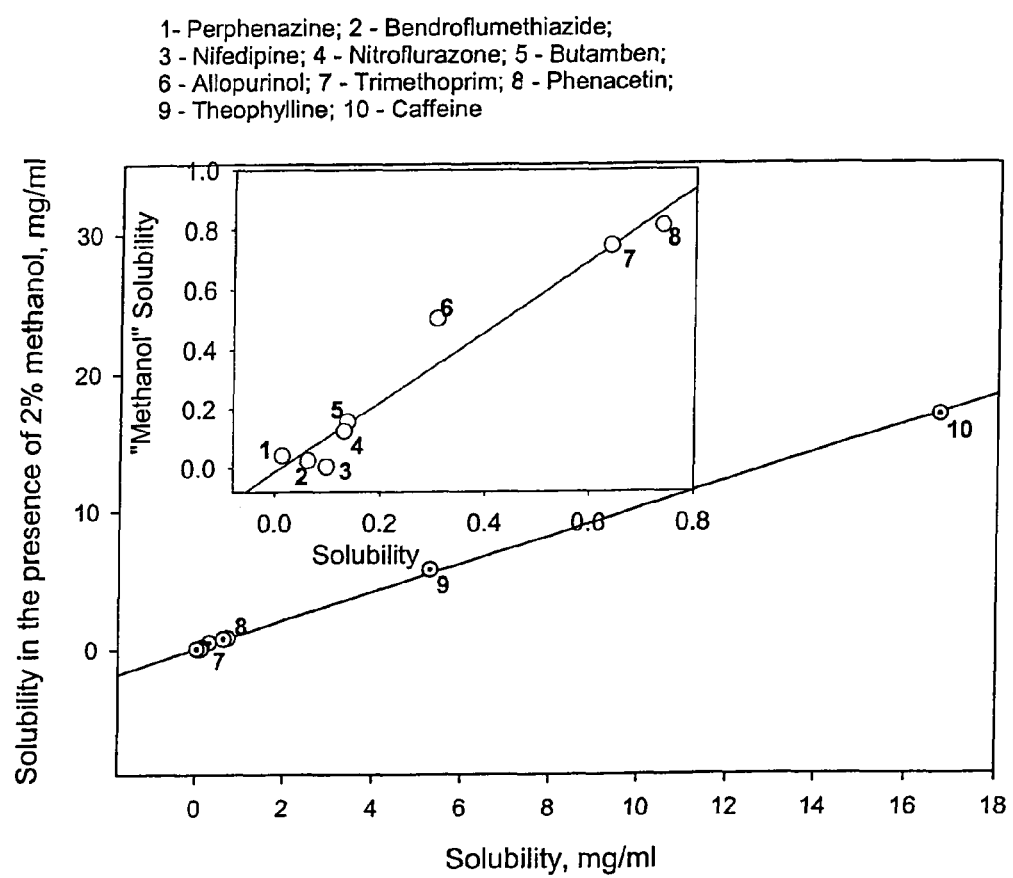
FIG. 6 illustrates the relationship between the solubility data in the presence of 2% methanol obtained for different compounds according to the present invention as measured by the total nitrogen content of the saturated solution and the solubility of the same compounds without DMSO.

The measured nitrogen content for each compound solution was transformed into concentration units, and the resulting experimental "methanol solubility" values are plotted in FIG. 6 versus corresponding data obtained for the same compounds in the same buffer using the procedure described in Example 2. The data given in FIG. 6 indicate clearly that there is a good correlation between the "methanol solubility" values obtained by the procedure and those obtained with dry compounds obtained by the procedure according to the present invention over the range from 1 µg/ml up to ca.20 mg/ml. The correlation between the data may be described by a linear relationship as:

$$S_{exp}^{MetOH}=0.055(\pm 0.047)+1.015(\pm 0.008)*S_{exp}$$

N=10; $r^2$=0.9994; s=0.1335, where $S_{exp}$ is the compound solubility measured experimentally by the procedure described; $S_{exp}^{MetOH}$—solubility of the compound measured in the presence of 2% methanol; N is the number of compounds; r—correlation coefficient, s—standard error of estimate.

The above correlation indicates clearly that the solubility of compounds examined in the presence of methanol generally exceeds that of the same compounds without methanol. However, the linear relationship observed can be used to re-calculate the measured solubility values from $S_{exp}^{MetOH}$ into $S_{exp}$ values, or can be used for ranking the solubility of a studied series of compounds.

This example illustrates the possibility to use the procedures according to the present invention for compounds dissolved in an organic solvent, such as methanol, for estimating the compound solubility in a given aqueous solution.

The results illustrated by the above examples demonstrate that the procedures according to the present invention facilitate high-throughput measurements of solubility for a wide variety of compounds.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method for determining the solubility of a solid compound in a solvent, the method comprising the steps of:
    (a) preparing a mixture of a quantity of the solid compound with a volume of the solvent;
    (b) incubating the mixture of the compound and the solvent to form a solution of the compound, whereby a first portion of the compound dissolves in the solvent to form the solution of the compound, and a second portion of the compound remains undissolved as a solid;

(c) removing the undissolved solid compound from the mixture, thereby providing a quantity of the solution of the compound;

(d) determining an amount of a constituent in the quantity of the solution of the compound resulting from (c), wherein the determination does not include a comparison of physical properties of one or more solutions containing known concentrations of the compound and physical properties of the solution of the compound; and (e) calculating solubility of the compound in the solvent by determining an amount of the compound dissolved in the quantity of the solution of the compound based on the determination of the amount of the constituent in (d).

2. The method of claim 1, wherein the quantity of the compound present in (a) is in excess of a maximum amount of the compound that can be dissolved in the solvent.

3. The method of claim 1, wherein the volume of the solvent present in (a) is insufficient to dissolve the quantity of the compound.

4. The method of claim 1, wherein the step of incubating the mixture of the compound and the solvent is continued until the quantity of the compound dissolved in the solvent is equal to a value equal to a percentage of an equilibrium solubility value of the compound in the solvent.

5. The method of claim 4, wherein the percentage of the equilibrium solubility value is selected from the group of values consisting of 5%, 10%, 15%, 20%, 25%, 30% 35%, 40%, 45%, 50%, 75%, 80%, 85% 90%, 93%, 95%, 96%, 97%, 98%, and 99%.

6. The method of claim 1, wherein the step of incubating the mixture of the compound and the solvent is continued until thermodynamically equilibrated phase separation of the compound from the solvent occurs.

7. The method of claim 6, wherein the quantity of the compound dissolved in the solvent after thermodynamically equilibrated phase separation occurs is equal to a value equal to a percentage of an equilibrium solubility value of the compound in the solvent.

8. The method of claim 7, wherein the percentage of the equilibrium solubility value is selected from the group of values consisting of 5%, 10%, 15%, 20%, 25%, 30%, 35%, 40%, 45%, 50%, 75%, 80%, 85%, 90%, 93%, 95%, 96%, 97%, 98%, and 99%.

9. The method of claim 1, wherein determining the amount of the constituent in the quantity of the solution of the compound resulting from (c) comprises determining an amount of a chemical element present in the compound.

10. The method of claim 9, wherein determining the amount of the chemical element present in the compound comprises determining the amount of the chemical element using a universal equimolar chemiluminescent nitrogen detector.

11. The method of claim 9, wherein determining the amount of the chemical element present in the compound comprises determining the amount of the chemical element using an equimolar chemiluminescent sulfur detector.

12. The method of claim 9, wherein determining the amount of the chemical element present in the compound comprises determining the amount of the chemical element using a total organic carbon detector.

13. The method of claim 1, wherein (d) comprises measuring overall content of a chemical element present in the compound after the compound has been dissolved in the solvent to produce the solution.

14. The method of claim 13, wherein (d) comprises measuring the overall content of the chemical element present in the compound and in the solvent.

15. The method of claim 13, wherein (d) comprises measuring the overall content of more than one chemical element present in the solution.

16. The method of claim 15, wherein at least one chemical element that is measured is present in the compound, and at least one chemical element that is measured is present in the solvent.

17. The method of claim 13, wherein the overall content of the chemical element is determined in a volume of the solution that is analytically determined.

18. The method of claim 17, wherein the volume of solution that is analytically determined is analytically determined using volumetric measurements.

19. The method of claim 17, wherein the volume of solution that is analytically determined is determined by determining an amount of the chemical element present in the solution.

20. The method of claim 1, wherein calculating the solubility of the compound in the solvent comprises converting overall content of a chemical element present in the solution into the amount of the compound.

21. The method of claim 20, wherein calculating the solubility of the compound in the solvent comprises using a quantitative relationship between the overall content of the chemical element and the amount of the compound in the quantity of solution.

22. The method of claim 1, wherein the quantity of the solution is determined by volumetric measurement.

23. The method of claim 1, wherein the quantity of the solution is determined by determining a quantity of a component within the solution.

24. The method of claim 23, wherein the component is a chemical element present in the solvent.

25. The method of claim 24, wherein the component is present in both the solvent and in the compound.

26. The method of claim 1, wherein the solvent is an aqueous solvent.

27. The method of claim 1, wherein the solvent is a nonaqueous solvent.

28. The method of claim 1, wherein the solvent is a mixture of a nonaqueous and an aqueous solvent.

29. The method of claim 28, wherein a percentage of the solvent is DMSO.

30. The method of claim 29, wherein the percentage of DMSO is selected from the group consisting of 0.1, 0.2, 0.3, 0.4, 0.5, 0.6, 0.7, 0.8, 0.9, 1.0, 1.2, 1.4, 1.6, 1.8, 2.0, 2.4, 2.8, 3.2, 3.6, 4.0, 4.5, 5, 7, 10, 15, 20, 25, 30, 35, 40, 45, 50, 55, 60, 70, 80, or 90.

31. The method of claim 1, wherein the compound contains a known quantity of a chemical element per unit of mass.

32. The method of claim 31, wherein the chemical element is selected from the group consisting of sulfur, carbon, nitrogen, hydrogen, phosphorus and oxygen.

33. The method of claim 1, wherein (a) comprises contacting the quantity of the compound with a volume of a first solvent to form a first mixture, and contacting a quantity of the first mixture with a volume of a further solvent to form the mixture of the quantity of the compound.

34. The method of claim 33, wherein the first solvent comprises an organic solvent.

35. The method of claim 34, wherein the organic solvent is DMSO.

36. The method of claim 33, wherein the compound is dissolved in the first mixture.

37. The method of claim 36, wherein the compound dissolved in the first mixture precipitates from solution when the first mixture is contacted with the further solvent.

38. The method of claim 33, wherein at least a portion of the first solvent is subsequently removed after forming the first mixture.

39. The method of claim 38, wherein the first solvent is removed by evaporation and/or by application of vacuum.

40. A method for determining the solubility of one or more solid compounds in one or more solvents, comprising preparing two or more mixtures of solid compounds and solvents and determining the solubility of each according to the method of claim 1.

41. The method of claim 40, wherein the two or more mixtures are each contained in a multi-well container.

42. The method of claim 41, wherein the multi-well container is a microtiter plate.

43. The method of claim 42, wherein the multi-well container has at least 4 wells.

44. The method of claim 43, wherein the multi-well container has at least 8 wells.

45. The method of claim 44, wherein the multi-well container has at least 16 wells.

46. The method of claim 45, wherein the multi-well container has at least 32 wells.

47. The method of claim 46, wherein the multi-well container has at least 48 wells.

48. The method of claim 47, wherein the multi-well container has at least 64 wells.

49. The method of claim 48, wherein the multi-well container has at least 80 wells.

50. The method of claim 49, wherein the multi-well container has at least 96 wells.

51. A method for determining the solubility of a solid compound in a solvent, the method comprising the steps of:
   (a) preparing a mixture of a quantity of the solid compound with a volume of the solvent;
   (b) incubating the mixture of the compound and the solvent to form a solution of the compound, whereby a first portion of the compound dissolves in the solvent to form the solution of the compound, and a second portion of the compound remains undissolved;
   (c) removing the undissolved compound from the mixture, thereby providing a quantity of the solution of the compound;
   (d) determining an amount of nitrogen and/or sulfur in the quantity of the solution of the compound resulting from (c) using a universal equimolar chemiluminescent detector;
   (e) calculating solubility of the compound in the solvent by determining an amount of the compound dissolved in the quantity of the solution of the compound, based on the determination of the amount of nitrogen and/or sulfur in (d).

52. A high-throughput method for determining the solubilities of a plurality of solid compounds, each in a solvent, the method comprising the steps of:
   (a) for each solid compound of a plurality of solid compounds, automatically dispersing the solid compound as a dry powder in a volume of a solvent;
   (b) incubating each of the mixtures of the respective compounds and the solvent to form a plurality of solutions of each compound, whereby a first portion of each of the compounds dissolves in the solvent to form the respective solutions of each of the compounds, and a second portion of each of the compounds remains undissolved;
   (c) removing the undissolved compounds from each of the mixtures, thereby providing a plurality of solutions for each of the compounds;
   (d) determining amounts of a constituent in each of the plurality of solutions resulting from (c), wherein the determinations do not include a comparison of physical properties of one or more solutions containing known concentrations of each respective compound and physical properties of the solution of each respective compound; and
   (e) calculating solubilities of each respective compound in the solvent by determining amounts of each compound dissolved in the respective solutions, based on the determination of the amounts of the constituent in (d).

* * * * *